United States Patent
Haenel et al.

(10) Patent No.: US 9,802,029 B2
(45) Date of Patent: Oct. 31, 2017

(54) MICRONEEDLE ARRANGEMENT AND ADAPTER

(71) Applicant: SANOFI-AVENTIS DEUTSCHLAND GMBH, Frankfurt am Main (DE)

(72) Inventors: Heinz Haenel, Frankfurt am Main (DE); Michael Schabbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 139 days.

(21) Appl. No.: 14/433,334

(22) PCT Filed: Oct. 1, 2013

(86) PCT No.: PCT/EP2013/070458
§ 371 (c)(1),
(2) Date: Apr. 2, 2015

(87) PCT Pub. No.: WO2014/053492
PCT Pub. Date: Apr. 10, 2014

(65) Prior Publication Data
US 2015/0231381 A1 Aug. 20, 2015

(30) Foreign Application Priority Data
Oct. 4, 2012 (EP) .................................. 12187313

(51) Int. Cl.
*A61M 5/00* (2006.01)
*A61M 37/00* (2006.01)

(52) U.S. Cl.
CPC ... *A61M 37/0015* (2013.01); *A61M 2037/003* (2013.01); *A61M 2037/0023* (2013.01)

(58) Field of Classification Search
CPC ........ A61M 5/34; A61M 5/345; A61M 5/346; A61M 5/347; A61M 5/348;
(Continued)

(56) References Cited

U.S. PATENT DOCUMENTS

| | | | | |
|---|---|---|---|---|
| 3,491,757 A | * | 1/1970 | Arce ...................... | A61M 5/34 604/242 |
| 2004/0054336 A1 | * | 3/2004 | Klint .................... | A61M 5/347 604/272 |

(Continued)

FOREIGN PATENT DOCUMENTS

| | | |
|---|---|---|
| JP | 58-194130 | 5/1982 |
| JP | 61-194644 | 5/1985 |

(Continued)

OTHER PUBLICATIONS

Extended European Search Report in Application No. 12187313.7, dated Apr. 23, 2013, 7 pages.

(Continued)

*Primary Examiner* — Emily Schmidt
(74) *Attorney, Agent, or Firm* — Fish & Richardson P.C.

(57) ABSTRACT

Described is a microneedle arrangement (1) comprising a body (2) having a proximal portion and a distal portion, a plurality of recesses (7) formed in proximal portion of the body (2), a microneedle array (5) disposed on the distal portion, and a connection needle (8) in fluid communication with the microneedle array (5) and extending proximally from the microneedle array (5). Further described is an adapter (9) comprising a coupling adapted to engage a medicament delivery device, an opening (14) adapted to receive the body (2), and a plurality of resilient latches (12) adapted to releasably engage the plurality of recesses (7) of the microneedle arrangement (1) when the body (2) is inserted into the opening (14).

21 Claims, 2 Drawing Sheets

(58) Field of Classification Search
CPC ...... A61M 2037/0023; A61M 37/0015; A61M 2037/003; A61M 2205/6045
See application file for complete search history.

(56) References Cited

U.S. PATENT DOCUMENTS

2010/0010455 A1* 1/2010 Elahi ................... A61M 5/3135
  604/208
2015/0038911 A1* 2/2015 Levin ...................... A61M 5/24
  604/173

FOREIGN PATENT DOCUMENTS

| WO | WO 2002/045771 | 6/2002 |
| WO | WO 2007/066341 | 6/2007 |
| WO | WO 2008/072229 | 6/2008 |
| WO | WO 2011/058548 | 5/2011 |

OTHER PUBLICATIONS

International Preliminary Report on Patentability in International Application No. PCT/EP2013/070458, issued Apr. 7, 2015, 5 pages.
International Search Report and Written Opinion in International Application No. PCT/EP2013/070458, dated Oct. 31, 2013, 8 pages.

* cited by examiner

MICRONEEDLE ARRANGEMENT AND ADAPTER

This application is a 371 U.S. National Application of PCT/EP2013/070458, filed on Oct. 1, 2013, which claims priority to European Patent Application Nos. 12187313.7, filed on Oct. 4, 2012, the entire contents of which are incorporated herein by reference.

TECHNICAL FIELD

The invention relates to a microneedle arrangement and an adapter for a medicament delivery device.

BACKGROUND OF THE INVENTION

Conventional medicament delivery devices for the treatment of diseases like diabetes require the patient to attach a needle assembly to the delivery device for each injection and remove the used needle assembly after the injection. These needles or needle assemblies are standardized to ensure they can be used for different types of delivery devices so that different suppliers can provide needles for patients in different countries. When subcutaneously administering different types of insulin, use of conventional needle assemblies leads to subcutaneous injections and typical profiles of bioavailability because the needles ensure a predetermined injection depth.

Conventional microneedles may be utilized for intradermal injection of drugs, e.g. rapid acting Insulin, which results in a non-typical action profile which is e.g. faster than in subcutaneous injections. However conventional microneedles are typically available only in patch-form, which are difficult to apply and remove from an injection site.

Thus, there remains a need for an improved microneedle arrangement and an adapter for a medicament delivery device.

SUMMARY OF THE INVENTION

Described is an improved microneedle arrangement and an adapter for a medicament delivery device.

In an exemplary embodiment, a microneedle arrangement according to the present invention comprises a body having a proximal portion and a distal portion, a plurality of recesses formed in proximal portion of the body, a microneedle array disposed on the distal portion, and a connection needle in fluid communication with the microneedle array and extending proximally from the microneedle array.

In an exemplary embodiment, the microneedle arrangement further comprises a grip plate arranged on the body and having an area extending radially beyond a cross-section of the body.

In an exemplary embodiment, the microneedle arrangement further comprises a first interface disposed on a proximal portion of the body and having a first contoured surface.

In an exemplary embodiment, the microneedle arrangement further comprises a needle base disposed on the distal portion and supporting the microneedle array.

In an exemplary embodiment, the body includes a first portion and a second portion arranged concentrically relative to the first portion, and the second portion includes the recesses.

In an exemplary embodiment, an adapter according to the present invention comprises a coupling adapted to engage a medicament delivery device, an opening adapted to receive the body, and a plurality of resilient latches adapted to releasably engage the plurality of recesses of the microneedle arrangement when the body is inserted into the opening.

In an exemplary embodiment, the coupling removably engages the medicament delivery device or is integrally formed with the medicament delivery device.

In an exemplary embodiment, the microneedle arrangement further comprises a second interface having a second contoured surface adapted to mate with the first contoured surface.

In an exemplary embodiment, the latches each include a protrusion adapted to engage a given recess. The latches have a deflected position abutting the body when the body is inserted into the opening and a non-deflected position when the protrusions are aligned with the given recesses. The protrusions and the recesses have corresponding ramped surfaces. When the microneedle arrangement is coupled to the adapter, rotation of the microneedle arrangement relative to the adapter causes the protrusions to disengage the given recesses and axial movement of the microneedle arrangement relative to the adapter due to interaction of the first interface and the second interface.

In an exemplary embodiment, the first interface and the second interface are corresponding cammed surfaces.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
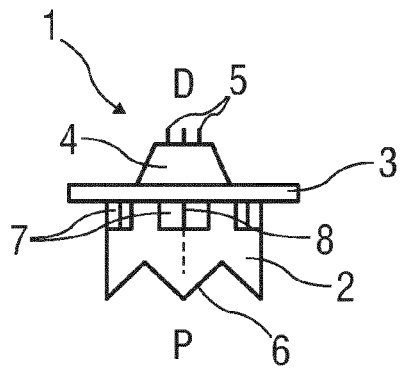
FIG. 1 is a longitudinal section of an exemplary embodiment of a microneedle arrangement.

FIG. 1 is a longitudinal section of an exemplary embodiment of a microneedle arrangement 1 according to the present invention. The microneedle arrangement 1 comprises a body 2 which may be cylindrical and hollow, although other geometries, sizes, shapes, materials and/or colors may be utilized. A grip plate 3 may be arranged on the body 2 for facilitating handling of the microneedle arrangement 1. The grip plate 3 may have an area extending beyond a cross-section of the body 2. For example, the grip plate 3 may have an oval shape, which allows the user to apply appropriate torque to the arrangement 1 without a danger of needle-stick. Proximal of the grip plate 3, a plurality of recesses 7 are circumferentially arranged in the body 2. A needle base 4, e.g. in the shape of a substantially frusto-conical protrusion, extends in a distal direction D from the grip plate 3. A microneedle array 5 may be disposed on the needle base 4. A connection needle 8, which is in fluid communication with the microneedles 5, extends proximally from the needle base 4 into the body 2. A proximal end of the body 2 may have a first interface 6 (e.g., a first contoured surface) adapted to engage a medicament delivery device. In the exemplary embodiment illustrated in FIG. 1, the first interface 6 has a toothing. A removable cap (not shown) may be coupled to the microneedle arrangement 1 (e.g., via the grip plate 3) for safety and facilitating attachment and removal.

Figure 2:
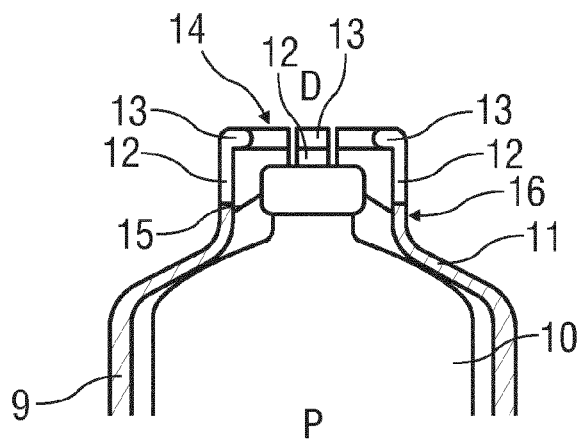
FIG. 2 is a longitudinal section of an exemplary embodiment of an adapter for a medicament delivery device.

FIG. 2 is a longitudinal section of a distal end of an exemplary embodiment of an adapter 9 for receiving a cartridge 10 containing a medicament to be delivered. In the exemplary embodiment, the adapter 9 may be coupled directly to the cartridge 10. In another exemplary embodiment, the adapter 9 may be removably coupled to a conventional medicament delivery device (e.g., a pen injector, an autoinjector, a syringe, etc.) by, for example, threads, snap-fit, friction, etc. In a further exemplary embodiment, the adapter 9 may be integrally formed with the medicament delivery device. For example, the adapter 9 may be formed as a distal end of the medicament delivery device.

In the exemplary embodiment shown in FIG. 2, the cartridge 10 may be supported within the adapter 9 by a shoulder 11 restricting relative motion of the cartridge 10 in the distal direction D. The adapter 9 comprises a neck portion 16 comprising a number of circumferentially arranged resilient latches 12 with respective radially inwardly directed protrusions 13. In an exemplary embodiment, the protrusions 13 are rounded off and/or ramped. The latches 12 extend in the distal direction D from the shoulder 11 and define a distal opening 14 through which the microneedle arrangement 1 may be inserted. The adapter 9 includes a second interface 15 (e.g., a second contoured surface complimenting the first contoured surface) adapted to engage the first interface 6 of the microneedle arrangement 1.

Figure 3:
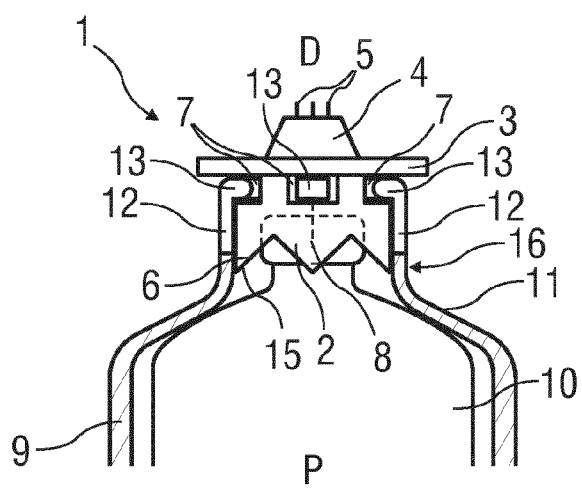
FIG. 3 is a longitudinal section of an exemplary embodiment of an adapter with a mounted microneedle arrangement.

FIG. 3 is a longitudinal section of an exemplary embodiment of microneedle arrangement 1 coupled to the adapter 9. To couple the microneedle arrangement 1 to the adapter 9, the body 2 is inserted through the distal opening 14 of the adapter 9. When the body 2 engages the protrusions 13, the latches 12 deflect radially outward to accommodate a diameter of the body 2. If, during this inserting movement, the first and second interfaces 6, 15 are aligned, the microneedle arrangement 1 will move axially toward the adapter 9. If the first and second interfaces 6, 15 are not aligned, there may be some rotational movement of the microneedle arrangement 1 relative to the adapter 9, along with axial movement. When the first and second interfaces 6, 15 are properly engaged, the protrusions 13 are aligned with the recesses 7, and the latches 12 return to a non-deflected position and engage the body 2. Also, when the first and second interfaces 6, 15 are properly engaged, the needle 8 pierces a septum (not illustrated) in the cartridge 10 for establishing a fluid communication between the cartridge 10 and the microneedle array 5.

In an exemplary embodiment, the microneedle arrangement 1 may be removed from the adapter 9 by pulling the microneedle arrangement 1 in the distal direction D off the adapter 9 or by rotating the microneedle arrangement 1 relative to the adapter 9. If the microneedle arrangement 1 is rotated relative to the adapter 9, the protrusions 13 disengage the recesses 7, and the ramped interaction between the first and second interfaces 6, 15 causes the microneedle arrangement 1 to be displaced axially from the adapter 9. In an exemplary embodiment, edges of the recesses 7 may be ramped to reduce a force necessary to disengage the protrusions 13.

Figure 4:
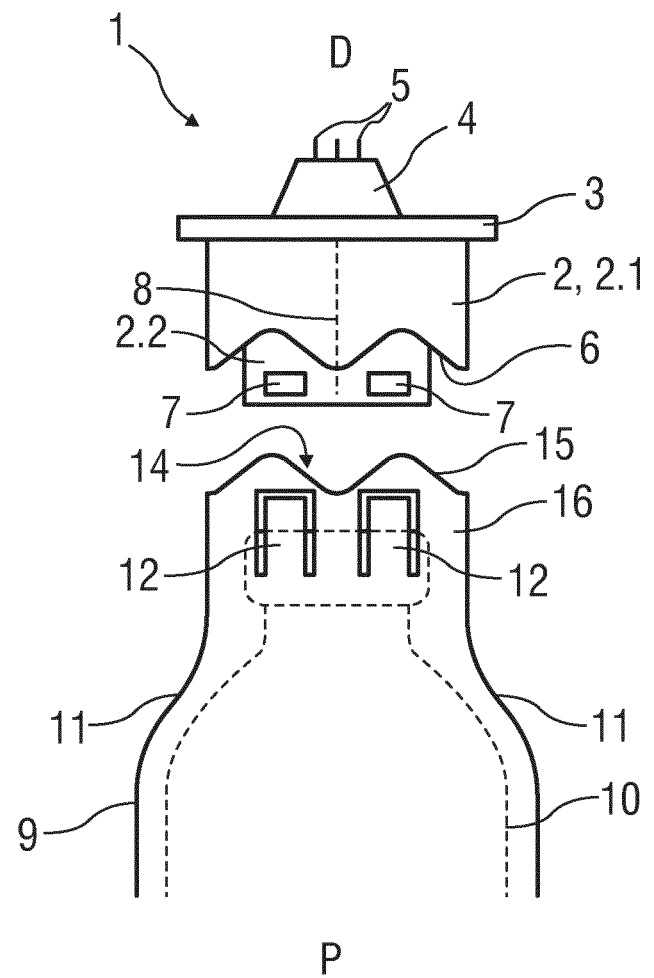
FIG. 4 is a longitudinal section of another exemplary embodiment of a microneedle arrangement and of another exemplary embodiment of an adapter.

FIG. 4 is a longitudinal section of another exemplary embodiment of a microneedle arrangement 1 and an adapter 9 according to the present invention. In this exemplary embodiment, the body 2 includes a first portion 2.1 and a second portion 2.2 concentrically arranged relative to the first portion 2.1 and including the recesses 7. The first portion 2.1 may have the first interface 6.

As shown in the exemplary embodiment in FIG. 4, the microneedle arrangement 1 may be coupled to the adapter 9 by inserting the microneedle arrangement 1 through the distal opening 14 of the adapter 9. When the inner portion 2.2 engages the latches 12, the latches 12 deflect radially until the protrusions are aligned with the recesses 7, thereby outwardly deflecting the flexible catch arms 12 which is facilitated by the rounded off inwardly directed protrusions of the catch arms 12. If, during this inserting movement, the first and second interfaces 6, 15 are aligned, the microneedle arrangement 1 will move axially toward the adapter 9. If the first and second interfaces 6, 15 are not aligned, there may be some rotational movement of the microneedle arrangement 1 relative to the adapter 9, along with axial movement. When the first and second interfaces 6, 15 are properly engaged, the protrusions 13 are aligned with the recesses 7, and the latches 12 return to a non-deflected position and engage the body 2. Also, when the first and second interfaces 6, 15 are properly engaged, the needle 8 pierces a septum (not illustrated) in the cartridge 10 for establishing a fluid communication between the cartridge 10 and the microneedle array 5.

The microneedle arrangement 1 may be removed from the adapter 9 by pulling the microneedle arrangement 1 in the distal direction D off the adapter 9 or by rotating the microneedle arrangement 1 relative to the adapter 9. If the microneedle arrangement 1 is rotated relative to the adapter 9, the protrusions 13 disengage the recesses 7, and the ramped interaction between the first and second interfaces 6, 15 causes the microneedle arrangement 1 to be displaced axially from the adapter 9. In an exemplary embodiment, edges of the recesses 7 may be ramped to reduce a force necessary to disengage the protrusions 13.

The needle base 4 may have any suitable shape, e.g. the shape of a cylinder, a truncated pyramid, a parallelepiped, a cube, etc.

The grip plate 3 and the needle base 4 may be considered parts of the body 2. For example, the grip plate 3 and the needle base 4 may be integrally shaped with the body 2.

The number of microneedles 5 in the microneedle arrangement 1 may be one or greater.

The microneedle arrangement 1 may for example be used for administering rapid acting insulin via intra-dermal injection through one to three microneedles 5.

The microneedle arrangement 1 and the adapter 9 with the mating interfaces 6, 15 may be used to distinguish a specific drug to be administered and to prevent administering the drug with an inappropriate needle.

In alternative embodiments the recesses 7 may be arranged in the adapter 9 while the corresponding latches 12 are arranged in the body 2 of the microneedle arrangement 1.

In alternative embodiments the latches 12 may likewise have radially outwardly directed protrusions 13 for engaging recesses in a cylindrical part such as the body 2, first portion 2.1, second portion 2.2 or adapter 9 which may be telescopable over the component having the latches 12.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A microneedle device comprising:
a body;
a first interface disposed on a first portion of the body and comprising a first contoured surface having a recessed portion angled relative to a longitudinal axis of the microneedle device;
a plurality of recesses formed in a second portion of the body concentrically arranged relative to the first portion, the second portion extending proximally beyond the first portion, wherein the recessed portion of the first contoured surface is configured to contact a second contoured surface of an adapter such that the microneedle device rotates relative to the adapter to align the recesses of the microneedle device with latches of the adapter when the recesses of the microneedle device are misaligned with the latches of the adapter;
a microneedle array disposed on a distal portion of the body; and
a connection needle in fluid communication with the microneedle array and extending proximally from the microneedle array along the longitudinal axis.

2. The microneedle device of claim 1, further comprising:
a grip plate arranged on the body, the grip plate having an area extending radially beyond a cross-section of the body transverse to the longitudinal axis.

3. The microneedle device of claim 2, wherein the recesses are arranged proximal relative to the grip plate.

4. The microneedle device of claim 2, wherein the grip plate is integrally shaped with the body.

5. The microneedle device of claim 1, wherein the first interface of the microneedle device is configured to engage a medicament delivery device, the medicament delivery device being being selected from the group consisting of a pen-injector, an auto-injector, and a syringe.

6. The microneedle device of claim 1, wherein the first interface is configured to engage with a second interface of an adapter, the adapter being configured to engage a cartridge containing a medicament and the second interface having the second contoured surface and being configured to mate with the first contoured surface.

7. The microneedle device of claim 6, wherein the needle is configured to establish fluid communication between the cartridge and the microneedle array when the first interface and the second interface are engaged.

8. The microneedle device of claim 1, further comprising:
a needle base disposed on the distal portion and supporting the microneedle array.

9. The microneedle device according to claim 8, wherein the needle base comprises a substantially frustoconical protrusion.

10. The microneedle device of claim 1, wherein the first contoured surface comprises alternating recessed portions and protruding portions extending circumferentially about the longitudinal axis of the microneedle device, the alternating recessed portions and protruding portions being configured to contact the second contoured surface of the adapter such that the microneedle device rotates relative to the adapter when the recesses of the microneedle device are misaligned with the latches of the adapter.

11. The microneedle device of claim 1, wherein a proximalmost end of the first portion of the body defines the first contoured surface, and the first contoured surface is configured contact a distalmost end of the adapter defining the second contoured surface.

12. An adapter comprising:
a shoulder configured to support a cartridge containing a medicament;
a plurality of resilient latches extending from the shoulder and defining an opening configured to receive a microneedle device, the microneedle device comprising:
a body,
a first interface disposed on a first portion of the body and comprising a first contoured surface;
a plurality of recesses formed in a second portion of the body, the second portion being concentrically arranged relative to the first portion and extending proximally beyond the first portion,
a microneedle array disposed on the body, and
a connection needle in fluid communication with the microneedle array and extending proximally from the microneedle array; and
a second interface disposed on a distal portion of the adapter and comprising a second contoured surface having a recessed portion angled relative to a longitudinal axis of the adapter, the recessed portion of the second contoured surface being configured to contact the first contoured surface of the microneedle device such that the adapter rotates relative to the microneedle device to align the latches of the adapter with the recesses of the microneedle device when the latches of the adapter are misaligned with the recesses of the microneedle device,
wherein the resilient latches are configured to releasably engage the recesses of the microneedle device when the body of the microneedle device is inserted into the opening.

13. The adapter of claim 12, wherein the shoulder is configured to support a medicament delivery device comprising the cartridge, the medicament delivery device being selected from the group consisting of a pen-injector, an auto-injector, and a syringe.

14. The adapter of claim 13, wherein the adapter removably engages the medicament delivery device or is integrally formed with the medicament delivery device.

15. The adapter of claim 12, wherein the needle is configured to establish fluid communication between the cartridge and the microneedle array when the first interface and the second interface are engaged.

16. The adapter of claim 12, wherein, if the body of the microneedle device is inserted into the adapter when the first interface and the second interface are not aligned, the microneedle device rotates relative to the adapter such that the first interface and the second interface can be properly engaged.

17. The adapter of claim 12, wherein the latches each include a protrusion configured to engage a given recess, and, when the microneedle device is coupled to the adapter, rotation of the microneedle device relative to the adapter causes the protrusions to disengage the given recesses and axial movement of the microneedle device relative to the adapter due to interaction of the first interface and the second interface.

18. The adapter of claim 17, wherein the latches are configured to be in a deflected position abutting the body when the body is inserted into the opening and to be in a non-deflected position when the protrusions are aligned with the given recesses.

19. The adapter of claim 12, wherein the second contoured surface comprises alternating recessed portions and protruding portions extending circumferentially about the longitudinal axis of the adapter, the alternating recessed portions and protruding portions being configured to contact the first contoured surface of the microneedle device such that the adapter rotates relative to the microneedle device when the latches of the adapter are misaligned with the recesses of the microneedle device.

20. A method of administering a medicament:
removably coupling an adapter to a cartridge containing the medicament;
engaging a first contoured surface disposed on a first portion of a microneedle device with a second contoured surface of the adapter such that a proximal facing recessed portion of the first contoured surface angled relative to a longitudinal axis of the microneedle device contacts a distal facing protruding portion of the second contoured surface angled relative to the longitudinal axis, thereby causing the adapter to rotate relative to the microneedle device such that recesses formed in a second portion of the microneedle device are aligned with latches of the adapter and to be removably coupled with the microneedle device such that fluid communication is established between a microneedle array of the microneedle device and the cartridge, wherein the second portion is concentrically arranged relative to the first portion of the microneedle device and extends proximally beyond the first portion of the microneedle device; and
administering an intra-dermal injection of the medicament from the cartridge through the microneedle array.

21. The method of claim 20, wherein the cartridge is disposed in a medicament delivery device, the medicament delivery device being selected from the group consisting of a pen-injector, an auto-injector, and a syringe.

* * * * *